(12) United States Patent
Piha et al.

(10) Patent No.: US 11,819,703 B2
(45) Date of Patent: Nov. 21, 2023

(54) ELECTROCARDIOGRAM (ECG) ELECTRODE WITH DEPOSITED INK RESISTIVE ELEMENT

(71) Applicant: West Affum Holdings Corp., Grand Cayman (KY)

(72) Inventors: Daniel R. Piha, Mercer Island, WA (US); Kenneth F. Cowan, Kirkland, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 124 days.

(21) Appl. No.: 17/164,432

(22) Filed: Feb. 1, 2021

(65) Prior Publication Data
US 2022/0080213 A1    Mar. 17, 2022

Related U.S. Application Data

(60) Provisional application No. 63/079,921, filed on Sep. 17, 2020.

(51) Int. Cl.
| | |
|---|---|
| *A61N 1/39* | (2006.01) |
| *A61B 5/361* | (2021.01) |
| *A61B 5/363* | (2021.01) |
| *A61B 5/00* | (2006.01) |
| *A61B 5/28* | (2021.01) |
| *A61N 1/04* | (2006.01) |

(52) U.S. Cl.
CPC .............. *A61N 1/3904* (2017.08); *A61B 5/28* (2021.01); *A61B 5/361* (2021.01); *A61B 5/363* (2021.01); *A61B 5/6805* (2013.01); *A61N 1/046* (2013.01); *A61B 2562/125* (2013.01); *A61B 2562/227* (2013.01); *A61N 1/0484* (2013.01)

(58) Field of Classification Search
CPC .... A61N 1/3904; A61N 1/046; A61N 1/0484; A61N 1/3968; A61B 5/28; A61B 5/361; A61B 5/363; A61B 5/6805; A61B 2562/125; A61B 2562/227; A61B 5/263
See application file for complete search history.

(56) References Cited

U.S. PATENT DOCUMENTS

| | | |
|---|---|---|
| 3,724,455 A | 4/1973 | Unger |
| 4,583,524 A | 4/1986 | Hutchins |
| 4,619,265 A | 10/1986 | Morgan et al. |

(Continued)

FOREIGN PATENT DOCUMENTS

| | | |
|---|---|---|
| EP | 3380189 B1 | 10/2018 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Eugene T Wu
(74) *Attorney, Agent, or Firm* — Columbia IP Law

(57) ABSTRACT

Technologies and implementations for a wearable medical device (WMD). The WMD includes electrocardiogram (ECG) electrodes and/or therapy electrodes having resistor components formed utilizing resistive ink.

18 Claims, 10 Drawing Sheets

(56) References Cited

U.S. PATENT DOCUMENTS

| | | | |
|---|---|---|---|
| 4,776,350 A * | 10/1988 | Grossman | A61N 1/046 607/152 |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bomn et al. | |
| 5,353,793 A | 10/1994 | Bomn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,618,208 A | 4/1997 | Crouse et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,586,038 B1 * | 3/2017 | Kosierkiewicz | B32B 7/12 |
| 9,592,403 B2 | 3/2017 | Sullivan | |
| 9,878,171 B2 | 1/2018 | Kaib | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0137688 A1 * | 6/2006 | Aisenbrey | A61N 1/0472 128/205.25 |
| 2006/0173499 A1 | 8/2006 | Hampton et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2019/0159696 A1 * | 5/2019 | Meeker | A61B 5/361 |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Wetting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Cado, et al., "Encircling Overlapping Multipulse Shock Waveforms for Transthoracic Defibrillation," JACC Journals, Dec. 1998, vol. 32 Issue 7, p. 2065-2071.

* cited by examiner

900 A computer program product

902 A signal bearing medium 904 at least one of
machine readable non-transitory medium having stored therein instructions that, when executed by one or more processors, operatively enable to:
  dispose a substrate on a base plate;
  disposing resistive ink on a surface of the substrate to form a resistor component of the ECG electrode;
  disposing a conductive electrode on the substrate;
  communicatively coupling the conductive electrode with the substrate;
  communicatively coupling an electric cable to the conductive electrode; and
  disposing a cover over the conductive electrode, the cover having a hole configured to expose the conductive electrode.

| 906 a computer-readable medium | 908 a recordable medium | 910 a communications medium |

Figure 9

ELECTROCARDIOGRAM (ECG) ELECTRODE WITH DEPOSITED INK RESISTIVE ELEMENT

RELATED APPLICATION

This application claims benefit of priority to U.S. Provisional Patent Application Ser. No. 63/079,921, filed on Sep. 17, 2020, titled ECG ELECTRODE WITH DEPOSITED INK RESISTIVE ELEMENT, which is incorporated herein by reference in its entirety for all purposes.

INFORMATION

Unless otherwise indicated herein, the approaches described in this section are not prior art to the claims in this application and are not admitted to be prior art by inclusion in this section.

Technology has contributed to improvements in healthcare. Some examples include healthcare related devices that may be mobile and personal. Mobile and personal healthcare devices may include Wearable Medical Devices (WMDs). Some WMDs may include medical devices that facilitate monitoring of various health related activities of a person. For example, a WMD may include a medical device that may be used to monitor a person's heart activity. The heart activity monitored by the WMD may be in the form of electrical signals (i.e., electrocardiogram or ECG). The WMD may be in a form factor capable of being worn by a person, whose heart activity is to be monitored. Monitoring of a person's ECG may facilitate intervention of heart related issues.

Some examples of WMDs, which may be used to monitor and facilitate therapy of a person's heart activity, may be a cardioverter defibrillator type medical device (e.g., wearable cardioverter defibrillator or WCD), Holter Monitor, etc. These example WMDs may include ECG electrodes configured to be attached to the person to receive the ECG signals. Because the ECG signals may correspond to electrical activities of the person's heart, the WMD including the ECG electrodes may include numerous electronic components to facilitate the monitoring and therapy of the person's heart.

All subject matter discussed in this section of this document is not necessarily prior art and may not be presumed to be prior art simply because it is presented in this section. Plus, any reference to any prior art in this description is not and should not be taken as an acknowledgement or any form of suggestion that such prior art forms parts of the common general knowledge in any art in any country. Along these lines, any recognition of problems in the prior art are discussed in this section or associated with such subject matter should not be treated as prior art, unless expressly stated to be prior art. Rather, the discussion of any subject matter in this section should be treated as part of the approach taken towards the particular problem by the inventor(s). This approach in and of itself may also be inventive. Accordingly, the foregoing summary is illustrative only and not intended to be in any way limiting. In addition to the illustrative aspects, embodiments, and features described above, further aspects, embodiments, and features will become apparent by reference to the drawings and the following detailed description.

SUMMARY

Described herein are various illustrative apparatus for an improved wearable medical device (WMD). Example apparatus may include wearable cardioverter defibrillator (WCD) having sensor electrodes, which may be utilized in monitoring and/or therapy devices (e.g., electrocardiogram or ECG electrodes in some WCDs, Holter Monitors, etc.) may include a resistor implemented utilizing resistive ink. In some examples, the resistive ink may be deposited on a surface of a substrate included in the electrodes, where the substrate may be a printed circuit board (PCB).

In some examples, the apparatus may be implemented to be utilized as a protection resistor in various high voltage applications. In other example, the apparatus may be implemented as part of various circuitry in a sensor electrode (e.g., electromagnetic interference or EMI filters, amplifiers, etc.).

Additionally, the present disclosure describes a method of manufacturing an improved a wearable medical device (WMD) having a sensor electrode including a resistor implemented utilizing resistive ink.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 9 illustrates an example computer program product arranged, in accordance with at least some embodiments described herein.

DETAILED DESCRIPTION

Figure 1:
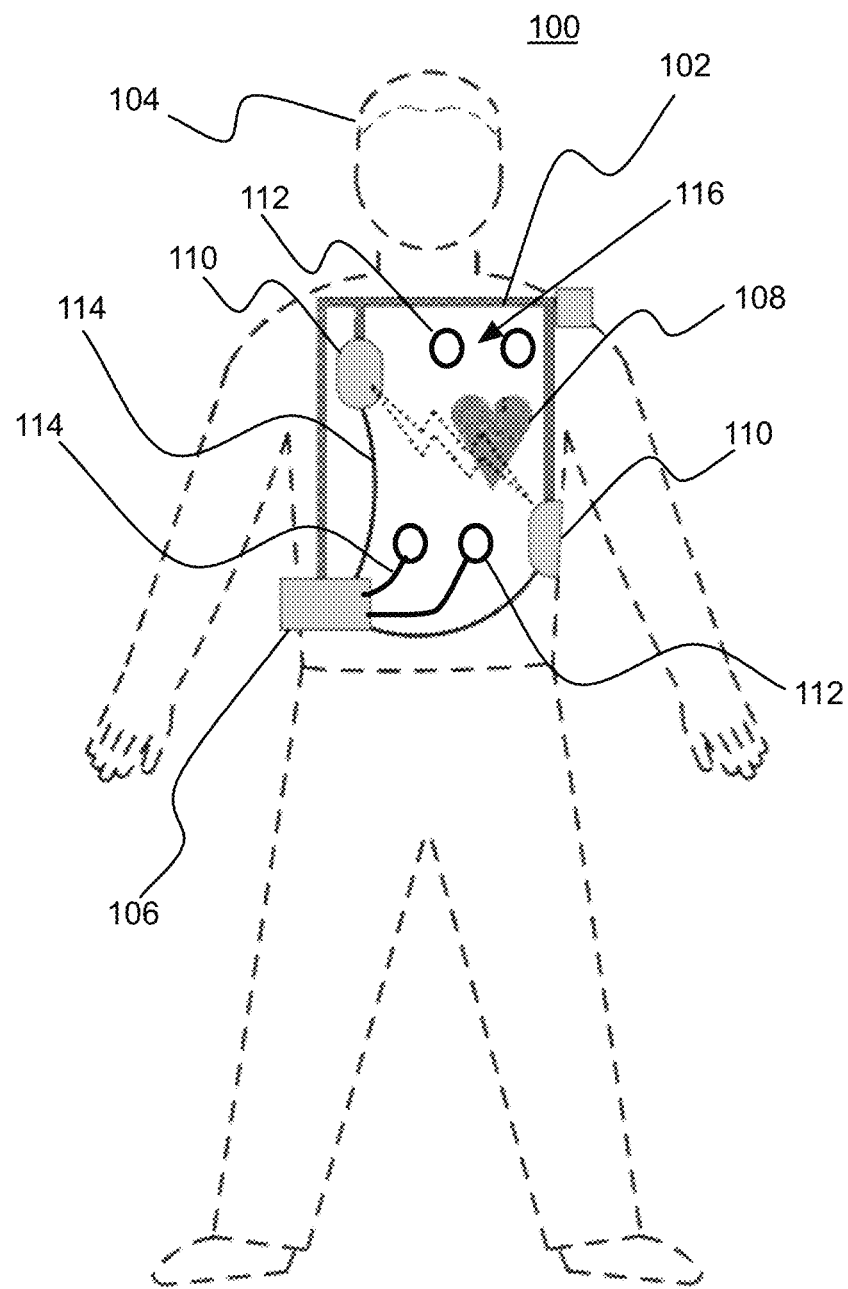
FIG. 1 illustrates an example system with which various embodiments of the present disclosure may be utilized.

The following description sets forth various examples along with specific details to provide a thorough understanding of claimed subject matter. It will be understood by those skilled in the art after review and understanding of the present disclosure, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to apparatus, systems, and methods related to a wearable cardioverter defibrillator (WCD) having electrodes with resistors implemented utilizing resistive ink.

A wearable medical device (WMD) may be used to facilitate monitoring and treatment of various medical conditions of a person. In order to facilitate monitoring and treatment of medical conditions of a person, a WMD may be worn by the person. In order to help facilitate the wearing of the WMD, the WMD that may be included in a support structure configured to be worn by the person, where the support structure may include various components of the WMD. An example of a WMD that may facilitate monitoring and treatment of a person may include a WMD configured to facilitate monitoring and treatment of potential issues with a person's heart (i.e., the person may have a health condition, where the electrical control system of the heart may malfunction, which may cause the heart to beat irregularly or not at all). Commonly, these types of WMDs may include a defibrillator device.

Briefly, the above problem with the rate of the heartbeat may be generally referred to as arrhythmia. Arrhythmia may be caused by many factors, but in general, arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to arrhythmia of some kind. Some arrhythmias may lead to a condition known as sudden cardiac arrest (SCA). In an SCA condition, the heart may fail to pump blood effectively, and as a result, death may occur.

An example type of arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amounts of blood or may not pump blood at all, which may eventually lead to death. Another type of arrhythmia, which may be associated with SCA, may be a condition known as ventricular tachycardia (VT).

Turning back WMDs, an electronic device may be utilized to help treat VF by defibrillating the heart. An example of this type of electronic device may be a defibrillator. A defibrillator may be capable of monitoring the electrical signals of the person's heart, and if necessary, administer treatment to the heart in the form of an electric shock. The defibrillator may monitor the electrical signals and provide the electric shock to the heart externally (i.e., through the surface of a body) via accessories commonly known as electrodes. The defibrillator may be in the form of a cardioverter defibrillator. As alluded to above, the cardioverter defibrillator may be included in a support structure configured to be worn by a person. (e.g., wearable cardioverter defibrillator or WCD), which may help facilitate monitoring the electrical activities of the person's heart and providing the electric shock to the heart in the VF condition. As a result, the WCD may help prevent Sudden Cardiac Death (SCD). The WCD may have a number of electrodes to facilitate monitoring of the electrical signals of the heart (e.g., rhythm of the heart) and a couple of electrodes to administer the electric shock as treatment/therapy. As part of the monitoring (e.g., arrythmia detection), the WCD may be configured to receive an electrocardiogram (ECG) signal from the number of electrodes (e.g., 5 ECG electrodes) on the skin of the person. In accordance with various embodiments of the present disclosure a resistor electronic component included in the electrodes may be implemented utilizing resistive ink.

Before turning to the figures, a non-limiting example configurations and utilization of the various embodiments of the present disclosure is described. In the non-limiting example, a wearable medical device (WMD) may be utilized to facilitate monitoring and treatment of a person, which may be a wearable cardioverter defibrillator (WCD). As the name of the defibrillator indicates, the WCD may be included in a wearable support structure (e.g., garment). This wearable garment, including the WCD, may be in wide variety of forms such as, but not limited to, vests, shirts, undergarments, t-shirts, etc.

As described above, the WCD may include a number electrodes to facilitate monitoring of electrical signals (ECG signal) via ECG electrodes from the person's heart and to facilitate an electric shock for the defibrillation process via defibrillator electrodes. Additionally, the WCD may include one or more electronic modules having many of the electronic components to facilitate the monitoring and/or the treatment of the heart (hereon, WCD monitor). The WCD monitor and the number of electrodes (e.g., ECG electrodes and defibrillator electrodes) may facilitate the monitoring the activities of the heart and the administration of the treatment/therapy of the heart (e.g., an electric shock for defibrillation, cardioversion and/or pacing). Accordingly, the electrodes may be disposed on the garment proximate to the person's heart and/or close to or on the skin of the person. In accordance with the present disclosure, these electrodes (e.g., ECG electrodes and/or defibrillator electrodes) may have its resistor electronic components implemented as resistive ink resulting in a smaller formfactor.

It should be appreciated that it is contemplated within the scope of the claimed subject matter that the disclosure herein includes both types of electrodes (ECG electrodes and/or therapy electrode), and accordingly, the remainder of the disclosure may be described with respect to an electrode. Continuing with the non-limiting example, an electrode may be formed with a conductive structure configured to contact the person's skin to facilitate monitoring the electrical signals of the person's heart and/or facilitating a therapy (e.g., defibrillating shock). The electrode may be an assembly of various components such as, but not limited to, a conductive electrode, a cover, an electrical cable, etc. In the non-limiting example, the electrode may include a substrate. A resistive ink may be disposed on the substrate to form an electronic resistor component for the electrode.

The resistive ink may be disposed on the substrate in a variety of manners such as, but not limited to, spin deposition, inkjet printing, chemical vapor deposition, etc. As may be appreciated, the electrode may have variety of shapes and sizes, and accordingly, the example components above may have corresponding variety of shapes and sizes such as, but not limited to, substantially circular, substantially rectangular, substantially oval, etc. Additionally, the deposition of the resistive ink itself may have a variety of shapes such as, but not limited to, substantially donut shape, substantially segmented shape, substantially spiral shape, and so forth. As may be appreciated, utilization of the resistive ink to form the resistor component of an electrode may help facilitate a wide variety improvements to a WCD.

Some examples of these improvements may include the reduction of the number of components during manufacturing of the electrode (e.g., a separate resistor component), which in turn may simplify a supply chain of manufacturing. The examples may include flexibility in the utilization of the substrate because the resistive ink may be deposited in a variety of 2 dimensional (2D) shapes as described herein. Some additional examples may include decreasing the overall thickness of an electrode assembly as compared to an electrode assembly having a separate resistor component. The utilization of the resistive ink to form the resistor component may help facilitate voltage management of the defibrillating pulse of a WCD. For example, having the resistor component located at the electrode (e.g., therapy electrode), may reduce the voltage from an externally applied defibrillation pulse from 5000V to a low clamp voltage such as, but not limited to, 5V at the electrode. This would be different than having a protection resistor at an ECG sensing circuit, which may include a cable between the electrode and the sensing circuit having a dielectric strength of 5000V. In some further examples, these improvements may include a conductive layer on a backside of the substrate may be electrically coupled to ground, which may result in a reduction of electrostatic noise pickup from the electrode. Additionally, it may be appreciated that the electrode having the resistive ink to form the resistor component may help facilitate a relatively small/thin form factor.

As alluded to above, the WCD monitor may comprise of various electronic components to facilitate operation of the WCD. For example, the WCD monitor may include a power supply such as, but not limited to, a battery to provide a defibrillator electrical shock to the person via the electrodes (e.g., therapy electrodes). Along with the battery, the WCD monitor may include one or more capacitors as part of a discharge circuit for the shock. Additionally, the WCD monitor may include a user interface such as, but not limited to, a physical button (e.g., response buttons), graphical user interface (e.g., display, interactive and non-interactive), audible interface (e.g., indication sounds), etc. The operation and coordination of the electronic components may be facilitated by a processor included in the WCD monitor being communicatively coupled to the various electronic components to facilitate operation of the WCD. It should be appreciated after review of this disclosure that the above example components are just a few examples, and accordingly, electronic components of a WCD monitor may include a wide variety of electronic components to facilitate operation of the WCD. Additionally, some of details of the WCD monitor will be described below.

It should be appreciated after review of this disclosure that the above non-limiting examples facilitate an improved electrode having an integrated resistor component formed utilizing resistive ink. This integration may facilitate various improvements as previously described.

Turning now to FIG. 1, FIG. 1 illustrates an example system with which various embodiments of the present disclosure may be utilized. In FIG. 1, a WMD may be configured to facilitate monitoring and treatment of a person's heart such as, but not limited to, a wearable cardioverter defibrillator (WCD) 100. The WCD 100 may be included in a support structure 102, which may be configured to be worn by a person 104. The WCD 100 may include various electronic components to facilitate the functionality of the WCD 100 as a heart monitoring and therapy (e.g., defibrillator) device. The various electronic components may be illustrated as a WCD module (hereon, a WCD monitor 106). The WCD 100 may include two defibrillator electrodes configured to defibrillate a person's heart 108, therapy electrodes 110, and a number of monitoring electrodes configured to detect and measure the person's electrical heart activity (e.g., electrocardiogram or ECG signals), ECG electrodes 112. As shown, the ECG electrodes 112 and the therapy electrodes 110 may be located proximate to the person's heart 108 and chest area 116. The ECG electrodes 112 and the therapy electrodes 110 may be communicatively coupled to the WCD monitor 106 via a number of electrical leads 114. As will be described in detail below, the ECG electrodes 112 and the therapy electrodes 110 may comprise of resistor components formed utilizing resistive ink.

It should be appreciated that the support structure 102 in FIG. 1 may be a variety of support structures such as, but not limited to clothing such as, but not limited to, a vest, a jacket, a t-shirt, a dress shirt, a belt, a blouse, a coat, and any combination thereof. Accordingly, the claimed subject matter is not limited in these respects.

In the present disclosure, when something is communicatively coupled, it should be appreciated that the term communicatively coupled may include electrical coupling, data coupling, thermal coupling, optical coupling etc. Accordingly, the term communicatively coupled may encompass a wide variety of coupling and is not limited in this respect.

Figure 2:
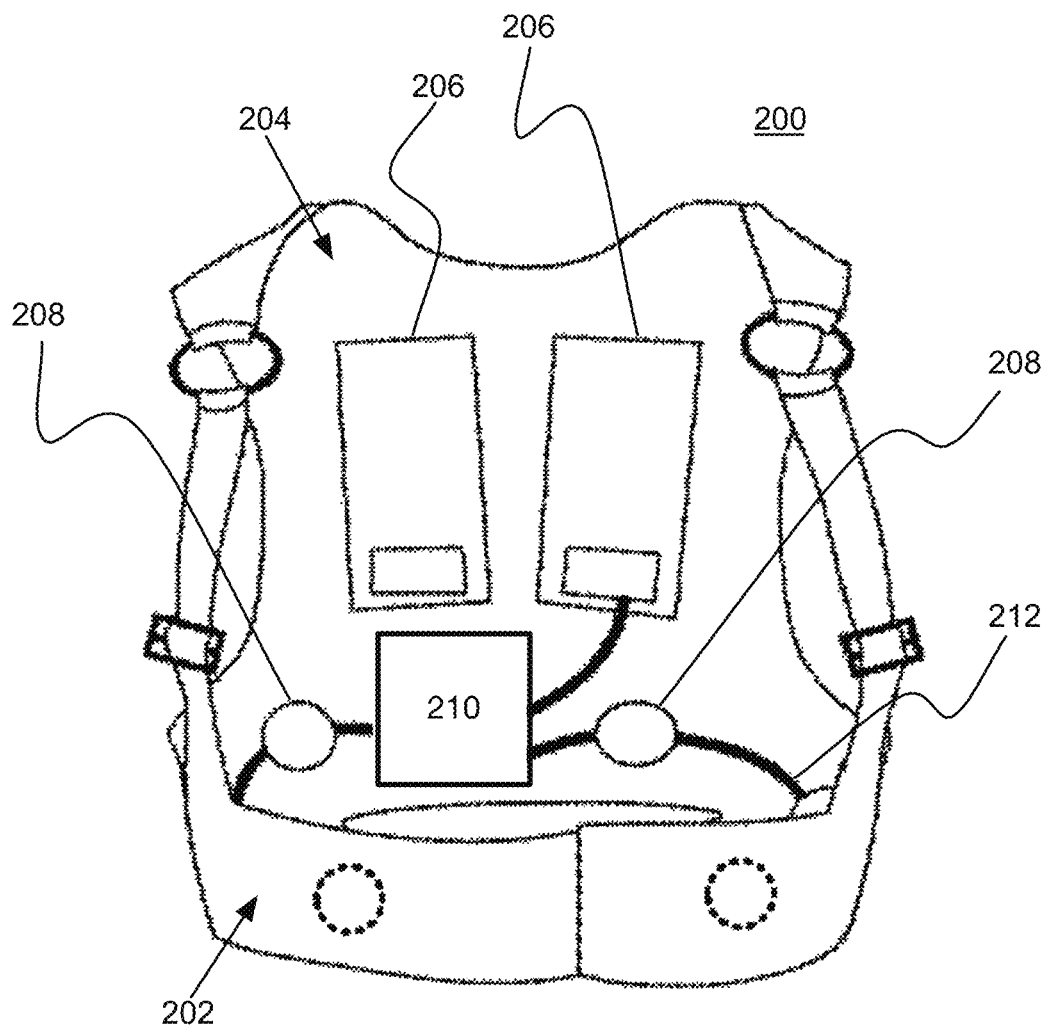
FIG. 2 illustrates an example of a wearable medical device (WMD) with which various embodiments of the present disclosure may be utilized.

FIG. 2 illustrates an example of a wearable medical device (WMD) with which various embodiments of the present disclosure may be utilized. In FIG. 2, a WCD 200 may be in the form of a clothing configured to be worn by a user such as, but not limited to, a vest type or a belt type clothing. Accordingly, the WCD 200 may have a front side 202 and a back side 204 forming the vest type WCD 200 as shown. Additionally, the WCD 200 may include one or more electrodes configured to defibrillate the person's heart, therapy electrodes 206 and one or more electrodes configured to detect and measure the person's electrocardiogram (ECG), ECG electrodes 208. It should be appreciated that the locations of the therapy electrodes 206 may be shown in various configurations such as, but not limited to, one front and one back, across a chest, across a back, etc. to facilitate defibrillation, and accordingly, the locations of the therapy electrodes 206 and/or the ECG electrodes 208 in FIG. 2 may be for illustrative purposes to show that there may be some electrodes to facilitate operation of the WCD 200. In the example shown in FIG. 2, the WCD 200 may include a WCD monitor 210 integrated with the WCD 200 on the back side 204. The WCD monitor 210 may be communicatively coupled to the therapy electrodes 206 and to the ECG electrodes 208 via one or more wires 212. This illustrates that the WCD may be located in a variety of locations.

The WCD monitor 210 may include various electronic components configured to facilitate operation of the WCD (i.e., various electronic components to facilitate monitoring and defibrillating the person's heart). For example, the WCD monitor 210 may include a power supply such as, but not limited to, a battery to provide a charge for a defibrillator shock via the therapy electrodes 206.

Having now described some of various systems in which the various embodiments may be utilized, the details of an electrode having a resistor electronic component formed utilizing resistive ink may be described.

Figure 3:
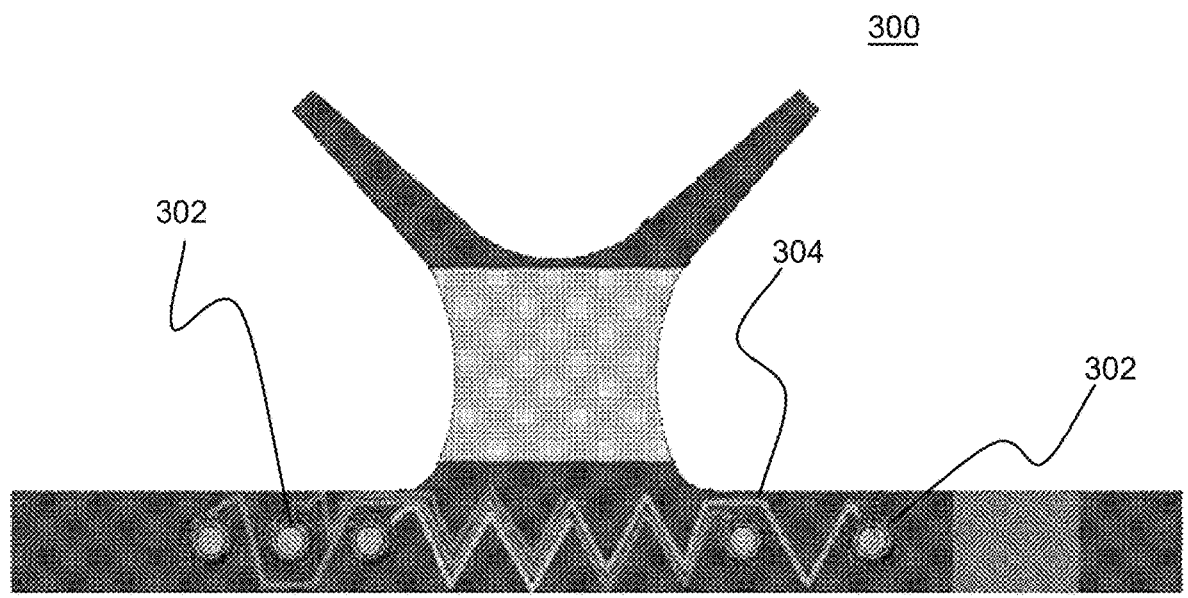
FIG. 3 illustrates a garment incorporating electrodes having resistor components formed utilizing resistive ink, in accordance with various embodiments.

FIG. 3 illustrates a garment incorporating electrodes having resistor components formed utilizing resistive ink, in accordance with various embodiments. In FIG. 3, a garment 300 (e.g., the support structure 102 shown in FIG. 1 and the WCD 200 shown in FIG. 2) may include electrodes 302. Additionally, the garment 300 may include some wiring 304 communicatively coupling the electrodes to a WCD monitor (e.g., the WCD monitor 106 of FIG. 1 and the WCD monitor 210 of FIG. 2). The electrodes 302 may be configured to contact a person's skin, and in some examples, may be configured to contact the person's skin utilizing various adhesive methodologies.

It should be appreciated that the electrodes 302 shown in FIG. 3 may be monitoring electrodes (e.g., ECG electrodes) and/or therapy electrodes (e.g., defibrillator electrodes). As mentioned above, the claimed subject matter may be described with respect to an electrode, which may be applicable to either monitoring electrodes and/or therapy electrodes. Accordingly, references may be made to an electrode, which may encompass both and either/or monitoring electrodes and/or therapy electrodes, and the claimed subject matter is not limited in this respect.

As previously alluded to, the shape of the electrodes 302 shown in FIG. 3 may be substantially round, but it should be appreciated that the shape of the electrodes 302 may be wide variety of shapes.

Figure 4:
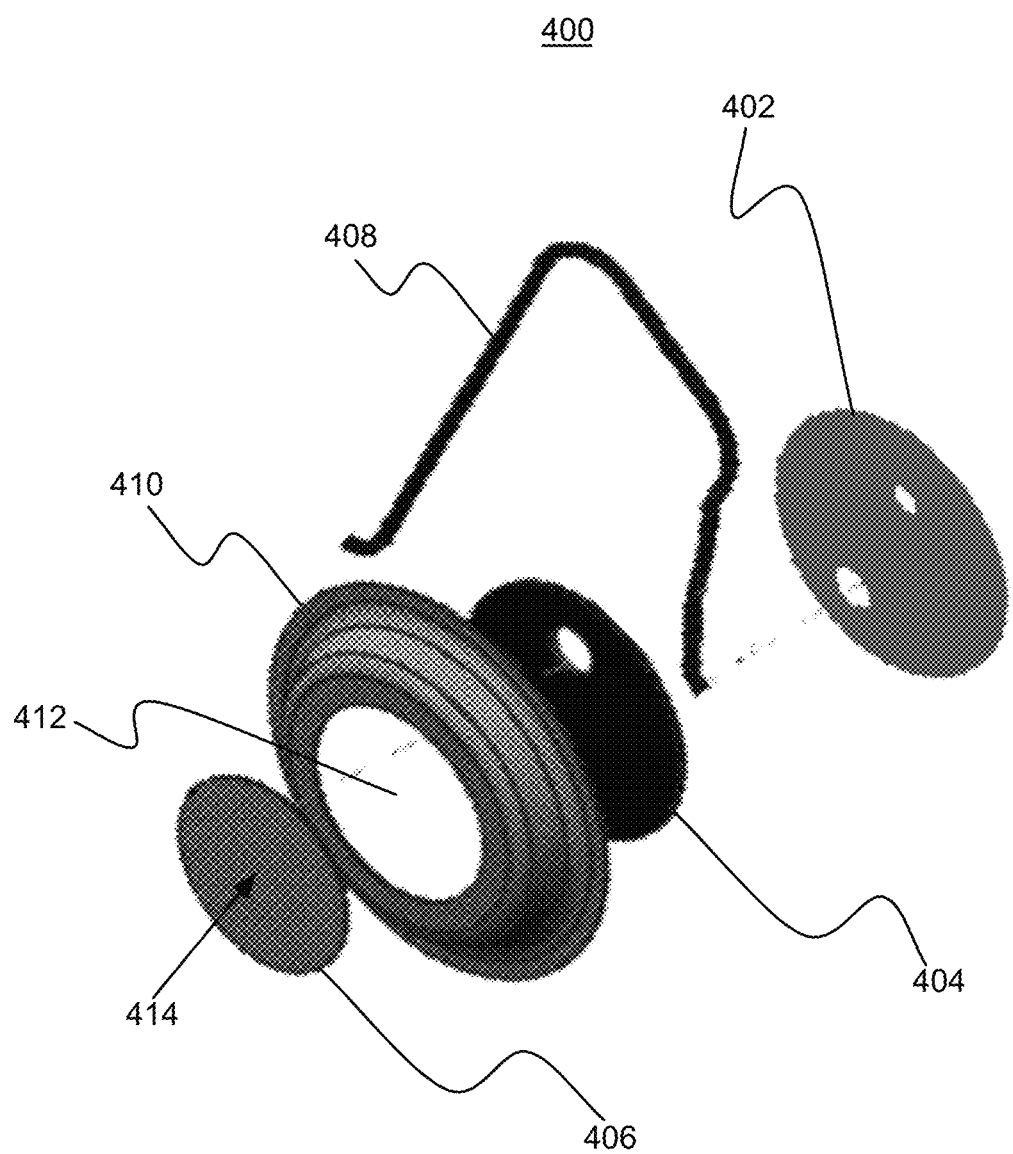
FIG. 4 illustrates an electrode having a resistor electronic component implemented utilizing resistive ink, in accordance with various embodiments.

FIG. 4 illustrates an electrode having a resistor electronic component implemented utilizing resistive ink, in accordance with various embodiments. In FIG. 4, an electrode assembly 400 may include a base plate 402, a substrate 404 disposed on the substrate 404, a conductive electrode 406 disposed on the substrate 404, an electric cable 408 communicatively coupled to the substrate 404, and a cover 410 disposed over the conductive electrode 404 and forming the electrode assembly 400. In accordance with various embodiments, the substrate 404 may include a resistor electronic component utilizing resistive ink.

Shown in FIG. 4, the cover 410 may have a hole 412 configured to expose a sensing portion 414 portion of the conductive electrode 406 (i.e., the sensing portion 414 configured to contact the person's skin to facilitate monitoring and/or therapy). Additionally, the electric cable 408 may be communicatively coupled to a WCD monitor (e.g., the WCD monitor 106 in FIG. 1 and the WCD monitor 210 in FIG. 2). As described, in one example, the WCD monitor may be configured to detect and treat one of ventricular fibrillation (VF) and/or ventricular tachycardia (VT) from electrocardiogram (ECG) signals via the electrode assembly 400 (e.g., 110 and 112 in FIG. 1, 206 and 208 in FIG. 2, and 302 in FIG. 3).

It should be appreciated that the electrode assembly 400 may include a wide variety of other components, which have been omitted to not obscure the present disclose subject matter and simplify the disclosure. Accordingly, the claimed subject matter is not limited in this respect.

Even though the shape of the electrode assembly 400 may be substantially round, it should be appreciated that the shape of the electrode assembly 400 may include a variety of shapes such as, but not limited to, substantially square, substantially rectangular, substantially oval, etc. Accordingly, the claimed subject matter is not limited in this respect. Even though the shape of the electrode assembly 400 may vary, it should be appreciated that the shape and configuration of the electrode assembly 400 may help facilitate management of the impedance and power capabilities of the electrode assembly 400.

Figure 5:
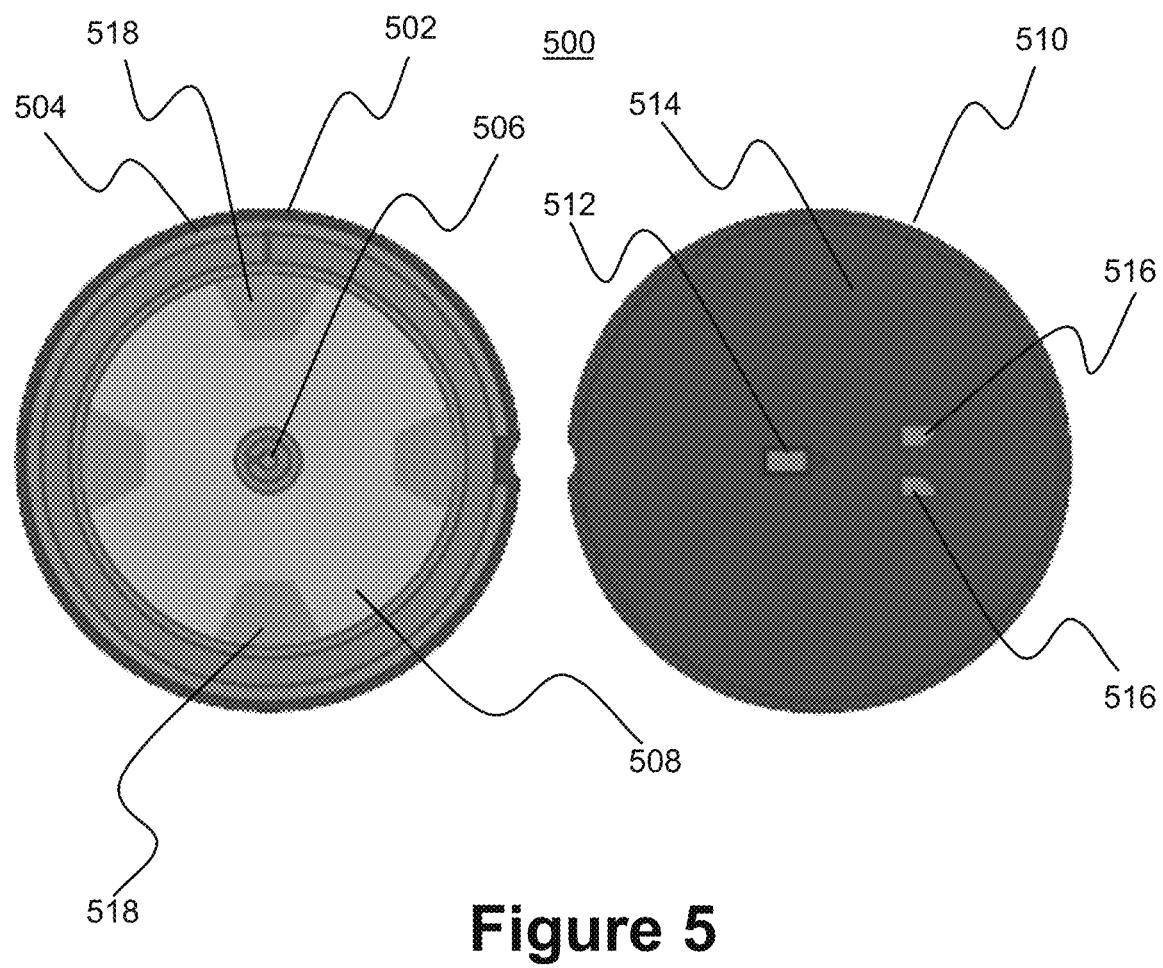
FIG. 5 illustrates two sides of an example of a resistor electronic component formed utilizing resistive ink, in accordance with various embodiments.

FIG. 5 illustrates two sides of an example of a resistor electronic component formed utilizing resistive ink, in accordance with various embodiments. In FIG. 5, a front side 502 (e.g., side on which a conductive electrode may be disposed) of a substrate 500 (e.g., the substrate 404 in FIG. 4) is shown. As shown, the substrate 500 may be of a substantially circular shape. The front side 502 may include a conductive ring 504, a via 506, and resistive ink 508 disposed on the front side 502. In FIG. 5, a back side 510 of the substrate 500 may include a center conductor pad 512, a solder mask 514, and a couple of conductive pads 516.

In FIG. 5, the conductive ring 504 may be configured to form a first terminal of a resistor electronic component with the center conductor pad 512 configured to form a second terminal of the resistor electronic component. In the example of FIG. 5, communicatively coupling the conductive ring 504 with the center conductor pad 512 may be facilitated by the via 506 configured to facilitate electrically coupling the first and second terminals of the resistor electronic component.

As shown in FIG. 5, the resistive ink 508 may be formed on the front side 502 of the substrate 500 in a substantially donut like configuration. The surface area of the resistive ink 508 may be managed by removing controlled amounts of the resistive ink 508 as shown by removed locations 518 on the front side 502 of the substrate 500. For example, an X-Y laser trimmer may be utilized to remove the resistive ink 508 to facilitate an increase in the resistance of the resistor electronic component up to a predetermined value in a manner that may maintain a high voltage capability of the resistor electronic components and does not create a relatively high current density areas that may reduce a pulse power capability of the electrode.

The conductive pads 516, shown on the back side 510 of the substrate 510 may be configured to communicatively couple to a ground shield for some examples. That is, in some examples, the back side 510 of the substrate 500 may be covered in some conductive material and communicatively coupled to a system ground to facilitate shielding and reduction of electric noise from electrostatic fields.

In some examples, the resistive ink 508 in FIG. 5 may be formed by depositing resistive ink on the front side 502 of the substrate 500 and managing the resistivity of the resistor electronic component by removing one or more portions of the deposited ink (e.g., by laser trimming) to achieve the desired resistance value.

In some examples, management of size, resistance, high voltage standoff, and energy of the electrode assembly 400 and its various components (e.g., the substrate 500) may be facilitated by configuration of the various components of the electrode assembly 400 and/or the various components of the substrate 500. For example, the distance between the conductive ring 504 and the center conductor pad 512 may be substantially maximized for the shape of the substrate 500, which may result in substantially maximizing the high voltage standoff and volume of the resistive ink 508 on the substrate 500. As may be appreciated, by substantially maximizing the volume of the resistive ink 508, the electrical resistance properties of the substrate 500 may be substantially minimized. Substantially minimizing the electrical resistance properties of the substrate 500 may facilitate higher quality ECG signals, however, will also lead to increased dissipation of energy in the resistor component (e.g., the substrate 500) when exposed to a high voltage such as, but not limited to, a defibrillating shock. Accordingly, the volume of the resistive ink 508 may be substantially maximized by utilizing substantially all of the potential area under the electrode (e.g., substrate 500).

In some examples, the distance between the conductive ring 504 and the center conductor pad 512 (i.e., distance between the first terminal and the second terminal of the resistor component) may be selected to increase the energy capabilities of the resistor electronic component of the substrate 500. For example, in order to facilitate prevention of potential arching when a high voltage (e.g., defibrillating shock) across the electronic resistor component of the electrode assembly 400, the distance between the conductive ring 504 and the center conductor pad 512 (i.e., distance between the terminal going to the body of the person and the terminal going to the ECG circuits) may be substantially maximized. Accordingly, the electrode assembly 400 may be shown with the electric cable 408 coupled at the center of the substrate 500 via the center conductive pad 512. As a result, by utilizing resistive ink, a resistor electronic component may be configured to withstand the high voltages and high energies of a WCD while providing the functionalities of a WCD electrode in a substantially smaller form factor. In FIG. 5, the conductive ring 504, the via 506, the center conductor pad 512, and conductive pads 516 may be made from a wide variety of conductive material and may itself be formed utilizing some form of ink (e.g., conductive ink). For example, the conductive material may include a wide variety of metals such as, but not limited to tin lead alloys, copper, gold, silver, platinum, aluminum, and so forth. As may be appreciated, it is contemplated within the scope of the claimed subject matter that the substrate 500 may be a printed circuit board (PCB) type substrate.

Figure 6:
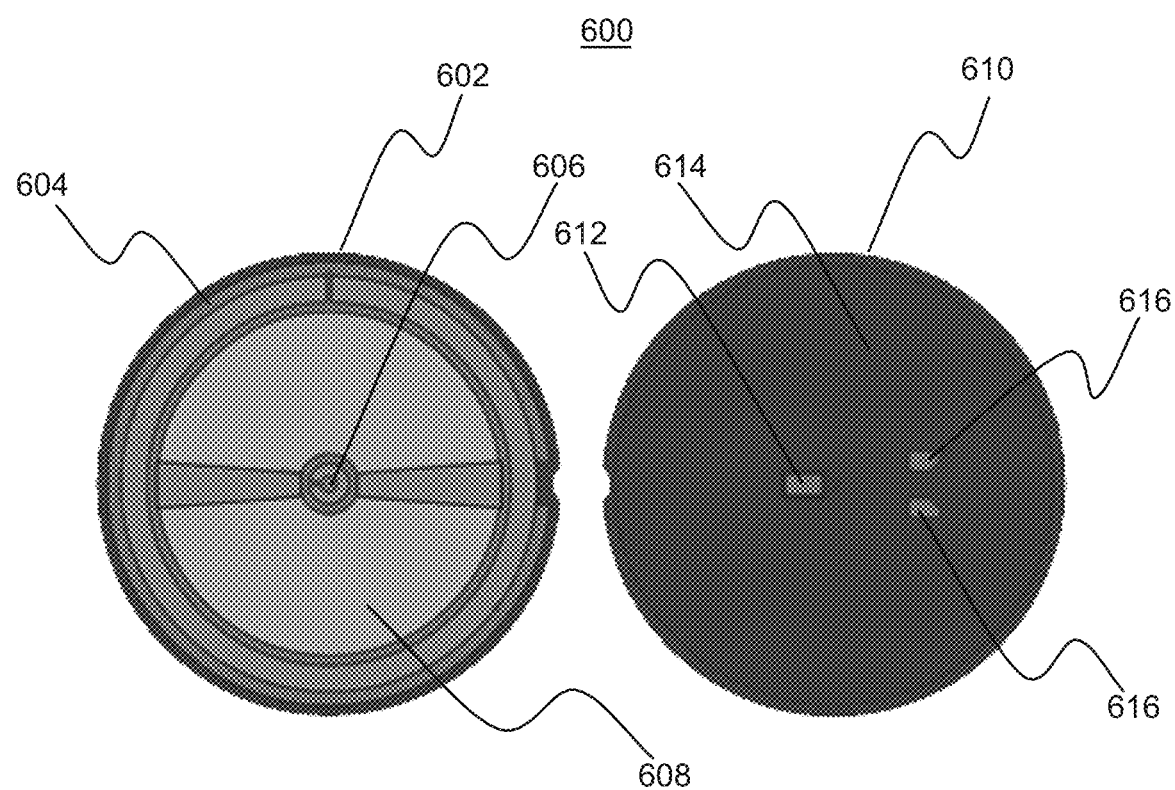
FIG. 6 illustrates two sides of another example of a resistor electronic component formed utilizing resistive ink, in accordance with various embodiments.

FIG. 6 illustrates two sides of another example of a resistor electronic component formed utilizing resistive ink, in accordance with various embodiments. In FIG. 6, a front side 602 (e.g., side on which a conductive electrode may be disposed) of a substrate 600 (e.g., the substrate 404 in FIG. 4) is shown. As shown, the substrate 600 may be of a substantially circular shape. The front side 602 may include a conductive ring 604, a via 606, and resistive ink 608 disposed on the front side 602. In FIG. 6, a back side 610 of the substrate 600 may include a center conductor pad 612, a solder mask 614, and a couple of conductive pads 616.

Similar to the substrate 500 shown in FIG. 5, the conductive ring 604 may be configured to form a first terminal of a resistor electronic component with the center conductor pad 612 configured to form a second terminal of the resistor electronic component. In the example of FIG. 6, communicatively coupling the conductive ring 604 with the center conductor pad 612 may be facilitated by the via 606 configured to facilitate electrically coupling the first and second terminals of the resistor electronic component.

As shown in FIG. 6, the resistive ink 608 may be formed on the front side 602 of the substrate 600 in a substantially segmented configuration. The substantially segmented configuration shown in FIG. 6 may facilitate flexibility in laser trimming the deposited resistive ink 608 to achieve a desired resistance.

It should be mentioned that management of resistance and energy of the electrode assembly 400 and its various components (e.g., the substrate 600) may be facilitated by configuration of the various components of the electrode assembly 400 and/or the various components of the substrate 600 as described above with respect to the substrate 500 in FIG. 5. For example, the distance between the conductive ring 604 and the center conductor pad 612 may be substantially maximized for the shape of the substrate 600, which may result in substantially maximizing the volume of the resistive ink 608 on the substrate 600. For example, the distance between the conductive ring 604 and the center conductor pad 612 (i.e., distance between the first terminal and the second terminal of the resistor component) may be selected to increase the energy capabilities of the resistor electronic component of the substrate 600.

Figure 7:
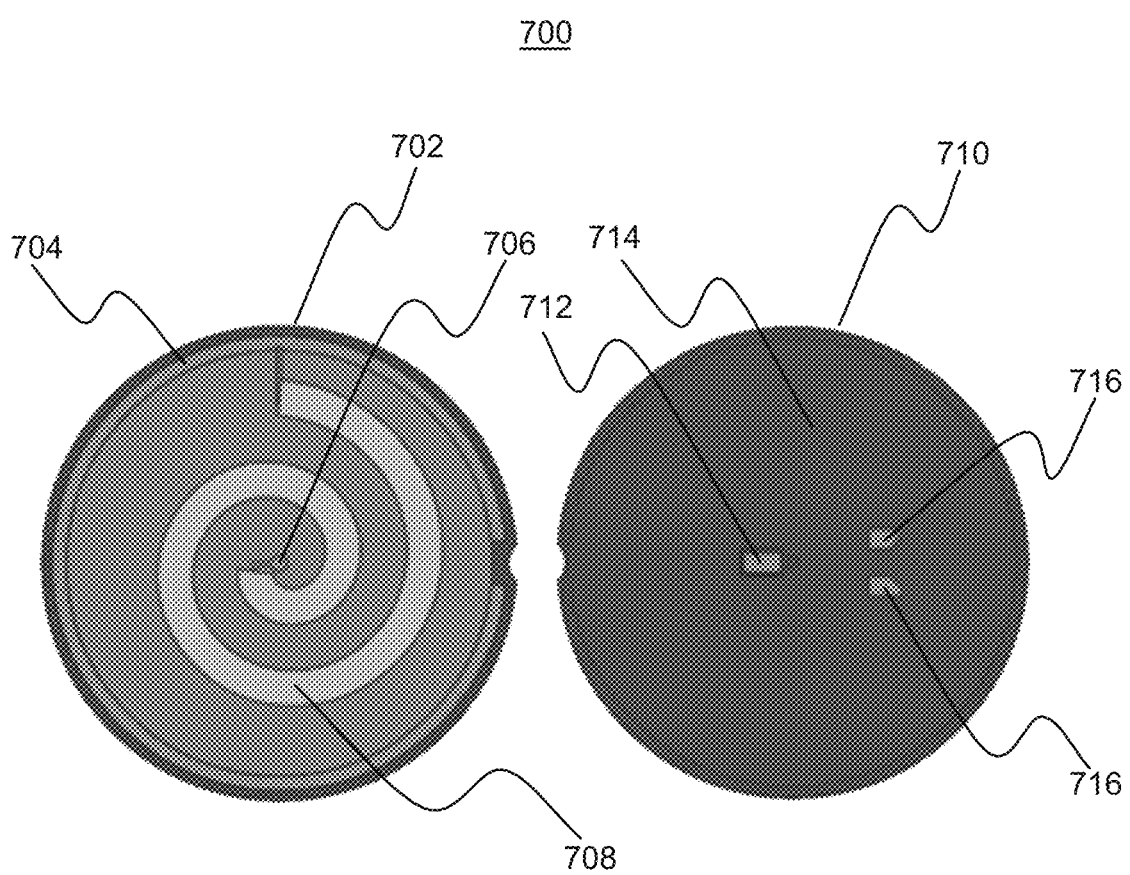
FIG. 7 illustrates two sides of another example of a resistor electronic component formed utilizing resistive ink, in accordance with various embodiments.

FIG. 7 illustrates two sides of another example of a resistor electronic component formed utilizing resistive ink, in accordance with various embodiments. In FIG. 7, a front side 702 (e.g., side on which a conductive electrode may be disposed) of a substrate 700 (e.g., the substrate 404 in FIG. 4) is shown. As shown, the substrate 700 may be of a substantially circular shape. The front side 702 may include a conductive ring 704, a via 706, and resistive ink 708 disposed on the front side 702. In FIG. 6, a back side 710 of the substrate 700 may include a center conductor pad 712, a solder mask 714, and a couple of conductive pads 716.

Similar to the substrates 500 shown in FIG. 5 and substrate 600 shown in FIG. 6, the conductive ring 704 may be configured to form a first terminal of a resistor electronic component with the center conductor pad 712 configured to form a second terminal of the resistor electronic component. In the example of FIG. 7, communicatively coupling the conductive ring 704 with the center conductor pad 712 may be facilitated by the via 706 configured to facilitate electrically coupling the first and second terminals of the resistor electronic component.

As shown in FIG. 7, the resistive ink 708 may be formed on the front side 702 of the substrate 700 in a substantially spiral configuration. Similar to the resistive ink 608 disposed in a substantially segmented configuration shown in FIG. 6, resistive ink 708 the substantially spiral configuration may facilitate flexibility in laser trimming the deposited resistive ink 708 to achieve a desired resistance. That is, it is contemplated within the scope of the disclosure that the shape and configuration of the deposited resistive ink on the substrate may be a wide variety based, at least in part, on the desired resistance value, power rating, parasitic reactance tolerances, mechanical properties (e.g., deposited on a flexible or stretchable substrate), etc. for a desired application. Accordingly, the claimed subject matter is not limited in this respect.

Here again, it should be mentioned that management of resistance and energy of the electrode assembly 400 and its various components (e.g., the substrate 700) may be facilitated by configuration of the various components of the electrode assembly 400 and/or the various components of the substrate 700 as described above with respect to the substrate 500 in FIG. 5. For example, the distance between the conductive ring 704 and the center conductor pad 712 may be substantially maximized for the shape of the substrate 700, which may result in substantially maximizing the volume of the resistive ink 708 on the substrate 700. For example, the distance between the conductive ring 704 and the center conductor pad 712 (i.e., distance between the first terminal and the second terminal of the resistor component) may be selected to increase the energy capabilities of the resistor electronic component of the substrate 600.

Figure 8:
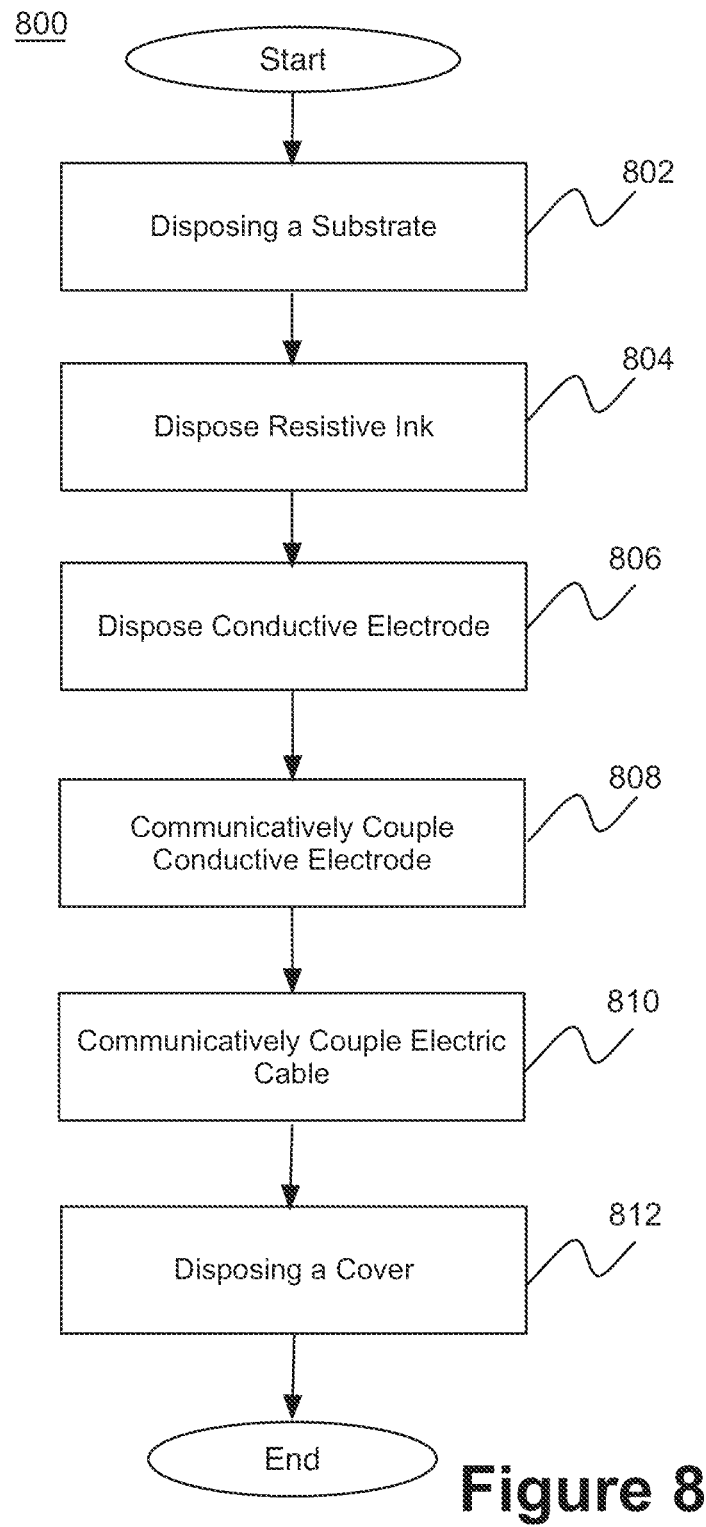
FIG. 8 illustrates an operational flow for making an electrocardiogram (ECG) electrode, arranged in accordance with at least some embodiments described herein.

FIG. 8 illustrates an operational flow for making an electrocardiogram (ECG) electrode, arranged in accordance with at least some embodiments described herein. In some portions of the description, illustrative implementations of the method are described with reference to the elements depicted in FIGS. 4-7. However, the described embodiments are not limited to these depictions. More specifically, some components depicted in FIGS. 4-7 may be omitted from some implementations of the methods detailed herein. Furthermore, other components not depicted in FIGS. 4-7 may be used to implement example methods detailed herein.

Additionally, FIG. 8 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 800 may be employed as part of making an electrode as described herein. Beginning at block 802 ("Disposing a Substrate"), a substrate may be disposed on a base plate (e.g., the base plate 404 in FIG. 4).

Continuing from block 802 to 804 ("Dispose Resistive Ink"), resistive ink may be disposed on a surface of the substrate to form a resistor electrical component of the electrode. The resistive ink may be disposed on a variety of manners and shapes. For example, the shapes disposed may be based, at least in part, on the desired resistance value, power rating, parasitic reactance tolerances, mechanical properties (e.g., deposited on a flexible or stretchable substrate), etc. for a desired application in accordance with various embodiments.

Continuing from block 804 to 806 ("Dispose Conductive Electrode"), a conductive electrode may be disposed on the substrate (e.g., front side of a substrate).

Continuing from block 806 to 808 ("Communicatively Couple Conductive Electrode"), the conductive electrode may be communicatively coupled with the substrate (e.g., on the front face of the substrate).

Continuing from block 808 to 810 ("Communicatively Couple Electric Cable"), an electric cable may be communicatively coupled with the substrate. Additionally, the electric cable may be communicatively coupled a cardioverter device (WCD) monitor, the WCD monitor being included in a support structure and configured to detect one of ventricular fibrillation (VF) and/or ventricular tachycardia (VT) from ECG signals.

Continuing from block 810 to 812 ("Disposing a Cover"), a cover may be disposed over the conductive electrode, where the cover may have a hole configured to expose the conductive electrode.

In general, the operational flow described with respect to FIG. 8 may be implemented as a computer program product, executable on any suitable computing system or the like. For example, a computer program product for determining an identity of a person based, at least in part, on stored correlated indications. Example computer program product may be described with respect to FIG. 9 and elsewhere herein.

FIG. 9 illustrates an example computer program product arranged, in accordance with at least some embodiments described herein. Computer program product 900 may include machine readable non-transitory medium having stored therein instructions that, when executed, cause the machine to make an electrode according to the processes and methods discussed herein. Computer program product 900 may include a signal bearing medium 902. Signal bearing medium 902 may include one or more machine-readable instructions 904, which, when executed by one or more processors, may operatively enable a computing device to provide the functionality described herein. In various examples, some or all of the machine-readable instructions may be used by the devices discussed herein.

In some examples, the machine readable instructions 904 when executed by one or more processors may dispose a substrate on a base plate. In some examples, the machine readable instructions 904 when executed dispose resistive ink on a surface of the substrate to form a resistor component of the ECG electrode. In some examples, the machine readable instructions 904 when executed may dispose a conductive electrode on the substrate. In some examples, the machine readable instructions 904 when execute may communicatively couple the conductive electrode with the substrate. In some examples, the machine readable instructions 904 when executed may communicatively couple an electric cable to the conductive electrode. In some examples, the machine readable instructions 904 when executed may dispose a cover over the conductive electrode, the cover having a hole configured to expose the conductive electrode.

In some implementations, signal bearing medium 902 may encompass a computer-readable medium 906, such as, but not limited to, a hard disk drive, a Compact Disc (CD), a Digital Versatile Disk (DVD), a digital tape, memory, etc. In some implementations, the signal bearing medium 902 may encompass a recordable medium 908, such as, but not limited to, memory, read/write (R/W) CDs, R/W DVDs, etc. In some implementations, the signal bearing medium 902 may encompass a communications medium 910, such as, but not limited to, a digital and/or an analog communication medium (e.g., a fiber optic cable, a waveguide, a wired communication link, a wireless communication link, etc.). In some examples, the signal bearing medium 902 may encompass a machine readable non-transitory medium.

In general, the methods described with respect to FIG. 9 and elsewhere herein may be implemented in any suitable computing system.

Figure 10:
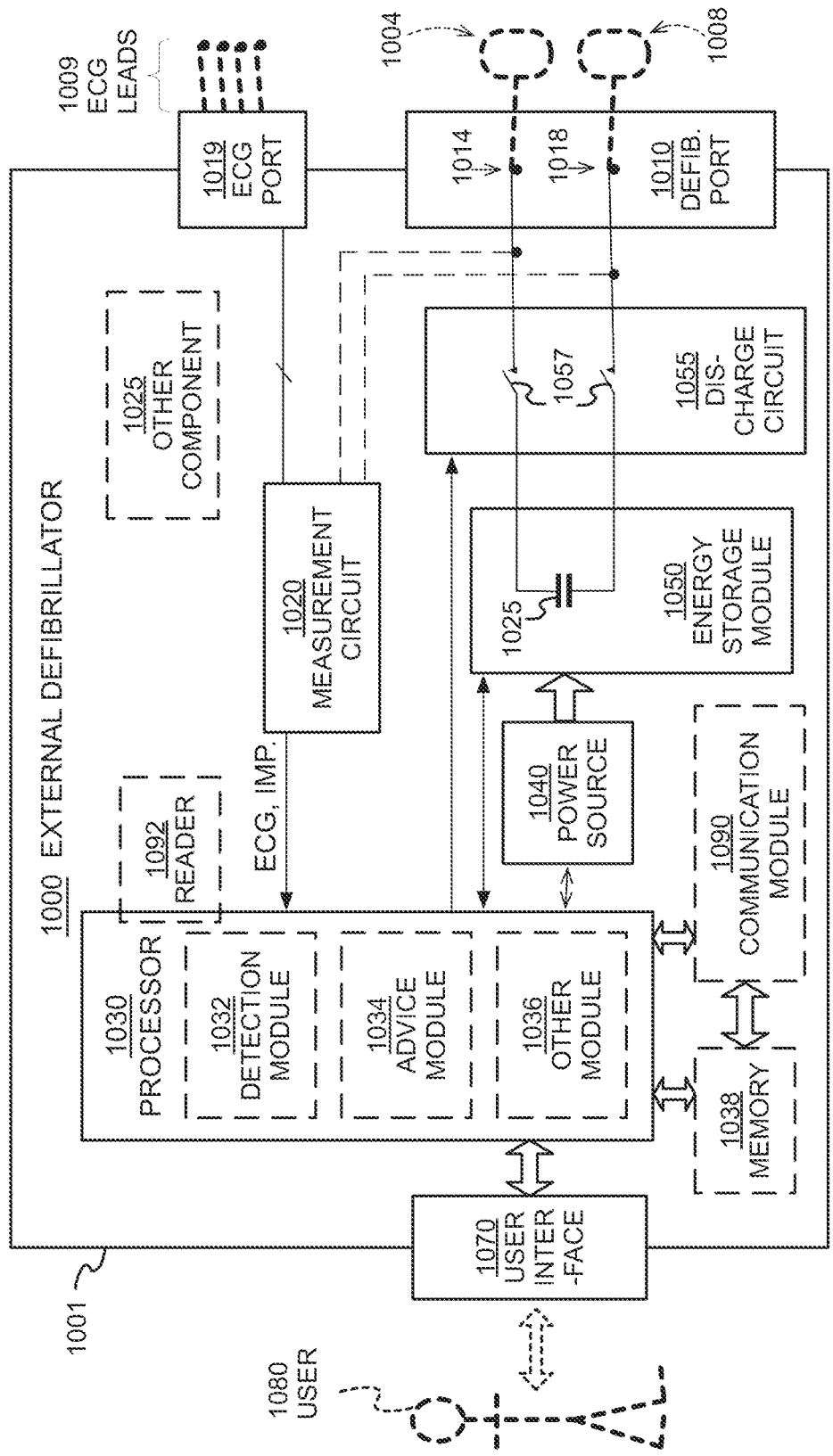
FIG. 10 is a block diagram illustrating components of a defibrillator device, which may be used with various embodiments.

FIG. 10 is a block diagram illustrating components of a defibrillator device, which may be used with various embodiments. These components may be, for example, components of a WCD 100, 200, and 300 (shown in FIGS. 1, 2, and 3).

The defibrillator device 1000 may be some of the above examples of a one or more modules for the WCD (e.g., WCD monitor 106 shown in FIG. 1 and WCD monitor 210 shown in FIG. 2) intended for use by a user 1080 (e.g., a wearer or person 104 shown in FIG. 1). The defibrillator device 1000 may typically include a defibrillation port 1010, such as a socket in housing 1001. The defibrillation port 1010 may include nodes 1014 and 1018. One or more electrodes 1004 and 1008, which may be plugged into the defibrillation port 1010, so as to make electrical contact with nodes 1014 and 1018, respectively. It may also be possible that the electrodes 1004 and 1008 may be connected continuously to the defibrillation port 1010, etc. Either way, the defibrillation port 1010 may be used for guiding via the electrodes 1004 and 1008 to a person 1004 an electrical charge that may have been stored in the defibrillator device 1000, as described herein.

The defibrillator device 1000 may also have an ECG port 1019 in the housing 1001, for receiving ECG cables 1009. The ECG cables 1009 may facilitate sensing of an ECG signal (e.g., a 12-lead signal or from a different number of lead signals). Moreover, a defibrillator-monitor could have additional ports (not shown), and the other component 1025 may be configured to filter the ECG signal (e.g., application of at least one filter to the signal to help facilitate removal of artifacts such as, but not limited to, chest compression due to chest compressions being delivered to the person).

The defibrillator 1000 also may include a measurement circuit 1020. The measurement circuit 1020 may receive physiological signals from the ECG port 1019, and also from other ports, if provided. The circuit 1020 may render detected physiological signals and their corresponding information. The information may be in the form of data, or other signals, etc.

If the defibrillator 1000 is configured as a WCD type device as described herein, ECG port 1019 may not be present. The measurement circuit 1020 may obtain physiological signals through the nodes 1014 and 1018 instead, when the electrodes 1004 and 1008 are attached to the person 1004. In these cases, a person's ECG signal may be detected as a voltage difference between the electrodes 1004 and 1008. Additionally, the impedance between the electrodes 1004 and 1008 may be detected, among other things, whether the electrodes 1004 and 1008 have been inadvertently disconnected from the person.

The defibrillator 1000 may also include a processor 1030. The processor 1030 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 1030 may include a number of modules. One example module may be a detection module 1032, which may detect outputs from the measurement circuit 1020. The detection module 1032 may include a VF detector. Accordingly, the person's detected ECG may be utilized to help determine whether the person is experiencing ventricular fibrillation (VF).

In another example module may be an advice module 1034, which may provide advice based, at least in part, on outputs of detection module 1032. The advice module 1034 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user, and prompt them to do it. In other examples, the defibrillator device may execute the advice by administering the shock. If the advice is to administer CPR, the defibrillator 1000 may further issue prompts for administrating CPR, and so forth.

The processor 1030 may include additional modules, such as module 1036 for various other functions. Additionally, if other component 1025 is provided, it may be operated in part by processor 1030, etc.

In an example, the defibrillator device 1000 may include a memory 1038, which may work together with the processor 1030. The memory 1038 may be implemented in a wide variety of manners. For example, the memory 1038 may be implemented such as, but not limited to, nonvolatile memories (NVM), read-only memories (ROM), random access memories (RAM), and so forth or any combination thereof. The memory 1038 may can include programs for the processor 1030, and so on. The programs may include operational programs execution by the processor 1030 and may also include protocols and methodologies that decisions may be made by advice module 1034. Additionally, the memory 1038 may store various prompts for the user 1080, etc. Moreover, the memory 1038 may store a wide variety of information (i.e., data) such as, but not limited to information regarding the person.

The defibrillator 1000 may also include a power source 1040. In order to facilitate portability of defibrillator device 1000, the power source 1040 may include a battery type device. A battery type device may be implemented as a battery pack, which may be rechargeable or not be rechargeable. At times, a combination of rechargeable and non-rechargeable battery packs may be utilized. Examples of power source 1040 may include AC power override, where AC power may be available, and so on. In some examples, the processor 1030 may control the power source 1040.

Additionally, the defibrillator device 1000 may include an energy storage module 1050. The energy storage module 1050 may be configured to store some electrical energy (e.g., when preparing for sudden discharge to administer a shock). The energy storage module 1050 may be charged from the power source 1040 to an appropriate level of energy, as may be controlled by the processor 1030. In some implementations, the energy storage module 1050 may include one or more capacitors 1052, and the like.

The defibrillator 1000 may include a discharge circuit 1055. The discharge circuit 1055 may be controlled to facilitate discharging of the energy stored in energy storage module 1050 to the nodes 1014 and 1018, and also to electrodes 1004 and 1008. The discharge circuit 1055 may include one or more switches 1057. The one or more switches 1057 may be configured in a number of manners such as, but not limited to, an H-bridge, and so forth.

The defibrillator device 1000 may further include a user interface 1070 for the user 1080. The user interface 1070 may be implemented in a variety of manners. For example, the user interface 1070 may include a display screen capable of displaying what is detected and measured, provide visual feedback to the user 1080 for their resuscitation attempts, and so forth. The user interface 1070 may also include an audio output such as, but not limited to, a speaker to issue audio prompts, etc. The user interface 1070 may additionally include various control devices such as, but not limited to, pushbuttons, touch display, and so forth. Additionally, the discharge circuit 1055 may be controlled by the processor 1030 or directly by the user 1080 via the user interface 1070, and so forth.

Additionally, the defibrillator device 1000 may include other components. For example, a communication module 1090 may be provided for communicating with other machines and/or the electrodes. Such communication may be performed wirelessly, or via wire, or by infrared communication, and so forth. Accordingly, information may be communicated, such as person data, incident information, therapy attempted, CPR performance, ECG information, and so forth.

It should be appreciated after review of this disclosure that it is contemplated within the scope and spirit of the present disclosure that the claimed subject matter may include a wide variety of healthcare devices. Accordingly, the claimed subject matter is not limited in these respects.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to the particular examples disclosed, but that such claimed subject matter also may include all implementations falling within the scope of the appended claims, and equivalents thereof.

What is claimed:

1. An electrocardiogram (ECG) electrode comprising:
   a base plate;
   a substrate disposed on the base plate, the substrate having resistive ink disposed on a surface to form a resistor component of the ECG electrode, wherein the substrate comprises the resistive ink having a substantially donut shape on the surface to form the resistor component of the ECG electrode;
   a conductive electrode disposed on the substrate and communicatively coupled to the substrate; and
   an electric cable configured to be communicatively coupled to the conductive electrode and to a wearable cardioverter device (WCD) monitor configured to detect one of ventricular fibrillation (VF) and/or ventricular tachycardia (VT) from ECG signals.

2. The ECG electrode of claim 1, wherein the base plate comprises an insulating base plate having holes configured to facilitate pass-through of the electric cable.

3. The ECG electrode of claim 1, wherein the substrate comprises a printed circuit board (PCB).

4. The ECG electrode of claim 3, wherein the PCB includes conductive components.

5. The ECG electrode of claim 4, wherein the conductive components comprise of copper pads coupled to vias.

6. An electrocardiogram (ECG) electrode comprising:
   a base plate;
   a substrate disposed on the base plate, the substrate having resistive ink disposed on a surface to form a resistor component of the ECG electrode, wherein the substrate comprises the resistive ink having a substantially donut shape on the surface to form the resistor component of the ECG electrode;
   a conductive electrode disposed on the substrate and communicatively coupled to the substrate;

an electric cable configured to be communicatively coupled to the conductive electrode and to a wearable cardioverter device (WCD) monitor configured to detect one of ventricular fibrillation (VF) and/or ventricular tachycardia (VT) from ECG signals; and a cover disposed over the conductive electrode, the cover having a hole configured to expose the conductive electrode.

7. The ECG electrode of claim 6, wherein the base plate comprises an insulating base plate having holes configured to facilitate pass-through of the electric cable.

8. The ECG electrode of claim 6, wherein the substrate comprises a printed circuit board (PCB).

9. The ECG electrode of claim 8, wherein the PCB includes conductive components.

10. The ECG electrode of claim 9, wherein the conductive components comprise of copper pads coupled to vias.

11. A wearable cardioverter device (WCD) comprising:
a support structure configured to be worn by a patient;
a WCD monitor coupled to the support structure, the WCD monitor configured to detect one of ventricular fibrillation (VF) and/or ventricular tachycardia (VT) from electrocardiogram (ECG) signals; and
an ECG electrode communicatively coupled to the WCD monitor, the ECG electrode comprising:
  a base plate,
  a substrate disposed on the base plate, the substrate having resistive ink disposed on a surface to form a resistor component of the ECG electrode, wherein the substrate comprises the resistive ink having a substantially donut shape on the surface to form the resistor component of the ECG electrode,
  a conductive electrode disposed on the substrate and communicatively coupled to the substrate,
  an electric cable communicatively coupled to the substrate and to the WCD monitor, and
  a cover disposed over the conductive electrode, the cover having a hole configured to expose a sensing portion of the conductive electrode.

12. The WCD of claim 11, wherein the WCD monitor comprises the WCD monitor included in the support structure.

13. The WCD of claim 11, wherein the support structure comprises a wearable garment configured to be worn by a person.

14. The WCD of claim 11, wherein the ECG electrode is further configured as a defibrillating shock delivery therapy electrode.

15. The WCD of claim 11, wherein the base plate comprises an insulating base plate having holes configured to facilitate pass-through of the electric cable.

16. The WCD of claim 11, wherein the substrate comprises a printed circuit board (PCB).

17. The WCD of claim 16, wherein the PCB includes conductive components.

18. The WCD of claim 17, wherein the conductive components comprise of copper pads coupled to vias.

* * * * *